Figure 1:
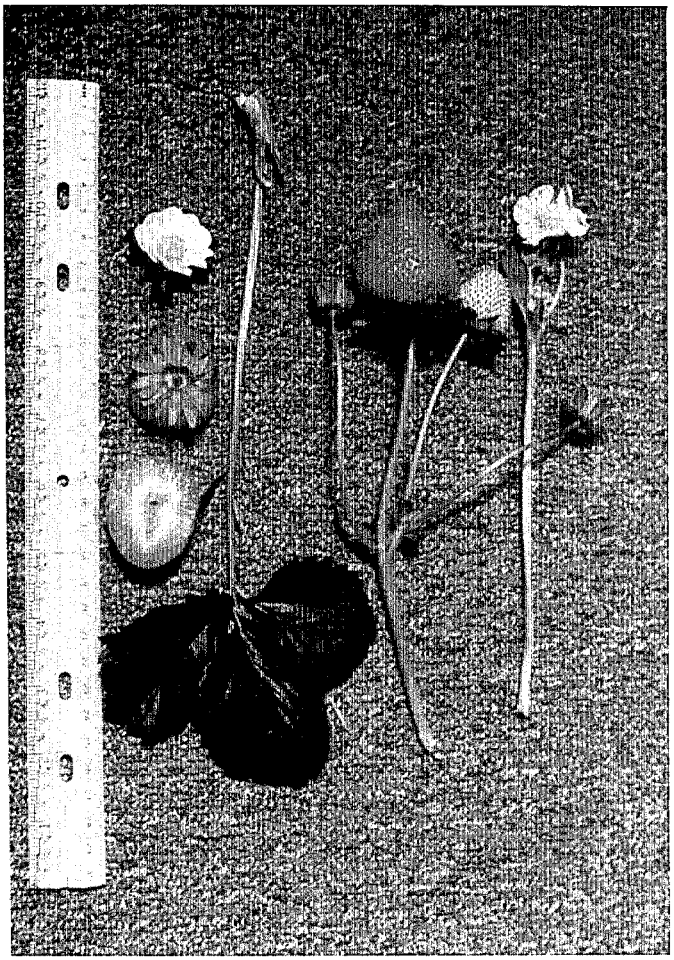

US00PP08970P

United States Patent [19]

Sjulin et al.

[11] Patent Number: Plant 8,970

[45] Date of Patent: Nov. 8, 1994

[54] STRAWBERRY PLANT CALLED 'X13'

[75] Inventors: Thomas M. Sjulin, Watsonville; Amado Q. Amorao, Camarillo; Joseph I. Espejo, Jr., Watsonville, all of Calif.

[73] Assignee: Driscoll Strawberry Associates, Inc., Watsonville, Calif.

[21] Appl. No.: 165,378

[22] Filed: Dec. 15, 1993

[51] Int. Cl.[5] ..... A01H 5/00

[52] U.S. Cl. ..... Plt./48

[58] Field of Search ..... Plt. 48, 49

[56] References Cited

PUBLICATIONS

Fogle, H. W., et al., (Listing for) 'Aroma', North American and European Fruit and Tree Nut Germplasm Resources Inventory, 1981, U.S.D.A., Prepared by Science and Education administration, Misc. Pub. No. 1406. p. 716.

*Primary Examiner*—James R. Feyrer

*Attorney, Agent, or Firm*—Townsend and Townsend Khourie and Crew

[57] ABSTRACT

This invention relates to a new distinct short day winter-planted variety of strawberry plant named 'X13'. The plant of this variety is distinguished by its dark, glossy foliage and its ability to initiate flowers from early spring to late fall in the Central Coast of California and spring and summer in southern California. The fruit is distinguished by its consistently high flavor, long shelf life, good fruit color inside and out and glossy, smooth surface. Its fruit is adapted to being processed for the freezer trade, especially for the Individual Quck Frozen berry demand, as well as for the fresh market.

1 Drawing Sheet

DESCRIPTION

This invention relates to a new distinct short day winter-planted spring-bearing variety of strawberry plant identified and designated as 'X13' which is a result of a cross of the unpatented variety known as Driscoll Strawberry Associates, Inc. (DSA) selection Z2 and the 'Joe Reiter' U.S. Plant Pat. No. 5,300. The variety is botanically identified as *F.* × *ananassa* Duch.

The seedlings resulting from the aforementioned cross were multiplied by stolon runners in Shasta County in a propagating nursery and other runner plants of each seedling clone were taken for testing to fruiting beds on the property of DSA. The runners from clones of the seedling held in Shasta County propagating nursery were set for further testing on the property of DSA. These tests indicated the merits of 'X13' and resulted in its selection as a promising test variety. Subsequent tests on DSA's Fly Ranch land proved that the variety had commercial value in California.

In the Drawing

FIG. 1 shows the plant parts of the new variety, typical in size, shape and color. The berry in cross section, illustrates flesh color and characteristic core cavity. The inflorescene illustrates typical branching and relative size during the middle of June.

The illustration shows two pedicels holding secondary berries and a pedicel holding one tertiary berry, and this is typical even as late as September. The primary berry may be wedge in shape with some longitudinal ribbing, but the symmetrical smooth conic berry in the illustration is typical as is the heavy shoulders with the calyx clasping the shoulders. The surface color is uniform over the entire surface and this is truce early in the year in contrast to the variety 'Chandler', U.S. Plant Pat. No. 5,262, whose shoulders are light in color when grown in southern California early in the spring. The petiole is typical and shows a bract present, but bracts are not always present. The flowers and calyx are typical with anthers producing an abundance of pollen.

The novel plant of 'X13' has wide adaptability having commercial value both in southern California and the central coast of California.

The plant of 'X13', in southern California is slightly smaller in size and darker in color than the 'Joe Reiter', U.S. Plant Pat. No. 5,300, in early spring, but will approach it in size by June and July. Its crown crop, the crop initiated at the nursery, is usually equal to the 'Joe Reiter' in earliness and production to the first of April, but its fruit size is not as large (see Table #1). One of its main attributes is its consistent good flavor which is as good as 'Joe Reiter' (Tables #2 and 3). This production is dependent on the fact that the variety is dug during October at a high elevation nursery where the proper chilling has occurred and is planted at the correct time.

Table #1 lists digging and planting dates and the production (Bon is a high-elevation nursery). Refractometer readings in Oxnard, Calif. during March gave 'X13' a rating of 9.9% soluble solids and 'Joe Reiter' 10.4%. Both of these ratings are considered high. Its other strong attribute is its fruit color inside and out and its outstanding shelf life due to its firm flesh and skin, as well as its attractive high gloss. In the oxnard district of southern California, it is capable of producing between June 27 and July 8, 560 grams per plant of superior quality fruit for the processing market. Its fruit character after being frozen has been rated high and it is especially attractive with good dessert qualities when frozen for individual quck frozen, I.Q.F. (the berries are frozen and marketed without being sliced).

'X13' is also distinguished from 'Joe Reiter' in southern California in that during March, individual central leaflets are not as long or as wide as 'Joe Reiter', and individual serrations are more acute at their apex than 'Joe Reiter'.

The fruit appearance is darker, has firmer skin and its shape doesn't become globular and rounded at the tips during the late spring crop as does 'Joe Reiter'. The isozymes in leaf extract vary from 'Joe Reiter' in that the PGI of 'Joe Reiter' is A4 and 'X13' is A2 (see Table

#5). It distinguishes itself from the 'Chandler' variety in southern California in that its plant and crop is later to develop and mature, its plant and leaflets are darker, its fruit is more uniform in color at maturity, its fruit surface is smoother and its flavor rates are superior (See Table #2).

In the central coast regions of California, even though 'X13' is a short day plant (not an everbearer), it has the ability to crop from April through October if the plant receives the correct chillign (as described above) before being planted. Table 190 4 gives the production by the month and year-end total as compared to the variety 'Swede' (DSA variety U.S. Plant Pat. No. 6,191). Its petioles are longer than 'Swede' (see Table #6). The plant size is larger than 'Swede' in September (see Table #7). Individual leaflets are similar in size and leaflet serrations are similar in depth to 'Swede' (see Table #6), but individual serrations are sharper (not as rounded) at their apex as are 'Swede's'. When given the same chilling before being planted, 'X13' produces more runners per plant than does 'Swede'. The total length of the inflorescence of 'X13' is longer than 'Swede' and thus produces its fruit for picking further from the crown than does 'Swede'. The average fruit size for the fruiting season is not as large as 'Swede', as there is a drop in size between the primary and secondary berries of the new variety. Primaries of the new variety can be large, as large as 'Swede', especially during the fall crop. Individual berries are firmer than 'Swede', and less prone to color unevenly around and shoulders. Both varieties have attractive berries with heavy shoulders and are conic to wedge in shape. The fruit of 'X13' is not as prone to produce short wedged fruit or folded, seedy split tips as does 'Swede' in the spring. Both varieties, however, produce an abundance of pollen even early in the spring. Both varieties have outstanding flavors and panels have rated them equal (see Table #3). One of the distinguishing differences in the two varieties is that the hair on pedicels of 'Swede' is perpendicular to the pedicel while 'X13' is irregularly parallel to the pedicel.

Tests have shown 'X13' to be susceptible to verticillium wilt, and angular leaf spot. Its fruit is susceptible to the anthracnose pathogen colletotrichum, but its plants show some tolerance. It has not been tested against phytophthora pathogens and it has not shown to be susceptible to the natural invasions of strawberry viruses common to the fruiting bed of California. It has not shown damage symptoms from pwdery mildew in the fruiting beds or in the nursery production increase plots. It has not been noticeably sensitive to the two-spotted mits infestations of California.

The varietal characteristics of the novel plant, described below in detail, were observed mainly during March, April and May in Oxnard (southern Calif.), and June and September in Watsonville (central Calif.). Both areas are coastal regions near the Pacific ocean. The color terminology is in accordance with the Munsell Color System.

SPECIFIC DESCRIPTION

Plant: Small and dark during early March in Oxnard, even when given necesssary chilling, but becoming larger during the fruiting season. Becoming large in Watsonville (see Table #7), often developing seven to eight crowns by end of the fruiting season. Considered a moderately high chilling variety requiring a moderate amount of chilling before being planted.

Leaves: The central leaflet, mostly medium in size in Oxnard during April, averaging 5.5 cm in width and 6 cm in length, but becoming larger in Watsonville during September, averaging 6.3 cm in width and 7.0 in length. Leaflets mostly held on the plant parallel to the soil surface. Serrations are moderately deep (see Table #6). It is common to have small double serrations present at the point werhe serrations join. The apex of serrations do become pointed, not rounded. Color of upper side of leaf in oxnard during March is 2.8G-2.0/4.4 and 1.5G-2.8/74 in Septemeber in Watsonville and the underside is 2.5 GY 4.3/7.1 in Watsonville. Petioles are short in Oxnard in March ranging from 10 to 13 cm (measuring from the bract that joins the crown to the petiolule) and increasing in length during the season and averaging 19 cm in length in Watsonville during September. Some bracts develop from the petioles. During periods, portions of the petioles may become purple. This purpling does not seem related to any pathogen and to the time this application is submitted these purple areas have not been detrimental to the plant growth. Petiolules of the central leaflet become long during September, October, Often over 20 mm, but averaging 10 mm. Table #5 gives the isozyme banding patterns compared to the 'Swede', 'Commander' and 'Joe Reiter' varieties.

Runners: Runners are vigorous and abundant at the nursery and excessive amounts can be produced at the fruiting bed if the plant is given more than adequate chilling before being planted.

Inflorescence: Crown crop inflorescences are medium in length, 18 cm, and by May in Oxnard, the average is 25 cm (measuring total length from the crown to extension of ripe berries). In Watsonville, by September, the total length average is 28.9 cm. The common peduncle is short in March in Oxnard, 4.5 cm in length, but increases to 14.6 cm average by September in Watsonville. The pedicel holding primary berries averages 8 cm and may be longer than this during the crown crop. The diameters of these pedicels vary from 2 to 3 mm. The pedicel holding primary berries may originate from the axil of two secondary peduncles or from one of the secondary peduncles. Pedicels holding secondary and tertiary berries are often fused together. A typical inflorescence contains a primary, two secondaries and one or two tertiaries. There is a noticeable drop in size between primary and secondary berries. The hair on pedicles is irregularly parallel to the pedicel. The flowers produce anthers with an abundance of pollen even during February in southern California. Petals from primary flowers average 5.9 in number and the average diameter of pistils of these flowers is 7.4 mm in diameter during September in Watsonville.

Fruit: The fruit surface is noticeably smooth, but the crown crop in march and the late September crop produces some ribbing and wedged fruit in outline with the length less than the width. During much of the crop, however, the primaries, secondaries and tertiaries produc symmetrical conic fruit. The short to medium wedged fruit (described in the USDA Bulletin 1043) has heavy shoulders with the calyx joining the fruit at a point within the outline of the fruit, so that sepals are unable to clasp the berry. Even symmetrical conic fruit has heavy shoulders, rarely necked. The surface is smooth with the seed slightly exerted to even with the surface. Ripe berries are uniform in color and have a good gloss. The flavor is consistently good (see Tables #2 and 3). There is a noticeable drop in size between primary and secondary fruit which often detracts from the fresh market appearance. The size of primary berries in Oxnard during March averages 46 mm in length and 40 mm in width. In Watsonville, during mid-summer, the size is less than in the spring, but in September and October, primary fruit size increases to an average of 43 mm in length and 42 mm in width. During this total production period, both the skin and flesh remain firm, giving the fruit an excellent shelf life with a good glossy appearance. The outside color of fruit varies from 6.3R-2.5/8.9 to 6.7R-3.5/13.1 and the flesh color is mostly 6.BR-3.7/15.8 to white around the core. This flesh color and internal flesh character gives a good appearance to the berry when frozen for processing. The aroma of the fruit is not as strong a fragrance as that of the 'Swede' variety. The seeds are small and yellow when not exposed to direct sun, mostly slightly exerted and are uniformly spaced and relatively close to each other (not having large unprotected skin surface areas between seeds).

Calyx: Medium to large, with the diameter of primaries reaching 50 mm, but averaging 41 mm. Individual sepals are mostly elliptical in outline averaging 16 in number during September with some overlapping, but most sepals do not have serrations present. Color of sepals facing fruit is 6.1GY-3.2/5.8.

TABLE #1

PRODUCTION AND FRUIT SIZE
1993 OXNARD TIME OF PLANTING,
OXNARD, CALIFORNIA

| PLOT | VARIETY | NURSERY | DIG DATE | PLANTING DATE |
|---|---|---|---|---|
| 406 | 'X13' | BON | 10/12/92 | 11/04/92 |

| | 1993 MAR | APR | MAY | TOTAL |
|---|---|---|---|---|
| NUMBER OF PICKS | 6 | 9 | 6 | 21 |
| GRAMS/PLANT | 113 | 199 | 175 | 486 |
| AVE. BERRY WT (gms./berry) | 26.4 | 26.4 | 20.4 | |

| PLOT | VARIETY | NURSERY | DIG DATE | PLANTING DATE |
|---|---|---|---|---|
| 1209 | REITER | BON | 10/12/92 | 11/04/92 |

| | 1993 MAR | APR | MAY | TOTAL |
|---|---|---|---|---|
| NUMBER OF PICKS | 7 | 9 | 6 | 22 |
| GRAMS/PLANT | 113 | 211 | 206 | 529 |
| AVE. BERRY WT (gms./berry) | 35.4 | 30.7 | 21.2 | |

Production and size yield data is from marketable berries only. This fruit is from plants that are winter planted, and in the first year production. Bon is a high elevation nursery.

TABLE #2

1993 OXNARD'S TIME OF PLANTING FLAVOR TEST SUMMARY

| EVALUATION DATE | # OF EVALUATORS | LEVEL OF SIGNIFICANCE | AVERAGE FLAVOR SCORE 'X13' | REITER | CHANDLER |
|---|---|---|---|---|---|
| 03/22/93 | 8 | 0.009** | 2.7 a | 3.1 a | 2.0 b |
| 04/01/93 | 14 | 0.000** | 3.1 a | 2.8 a | 2.1 b |
| 04/08/93 | 15 | 0.000** | 3.5 a | 3.8 a | 2.3 b |
| 04/15/93 | 11 | 0.108 | 3.3 | 3.0 | 2.7 |
| 04/22/93 | 10 | 0.470 | 3.4 | 2.9 | 2.9 |
| 04/29/93 | 13 | 0.035* | 2.9 ab | 3.4 a | 2.5 b |
| 05/07/93 | 10 | 0.182 | 2.7 | 3.5 | 2.7 |
| 05/14/93 | 9 | 0.890 | 3.1 | 3.3 | 3.3 |
| 05/21/93 | 9 | 0.831 | 3.6 | 3.2 | 3.4 |

TABLE #2-continued

1993 OXNARD'S TIME OF PLANTING FLAVOR TEST SUMMARY

| EVALUATION DATE | # OF EVALUATORS | LEVEL OF SIGNIFICANCE | AVERAGE FLAVOR SCORE 'X13' | REITER | CHANDLER |
|---|---|---|---|---|---|
| | | AVERAGE: | 3.1 | 3.2 | 2.7 |

**Significantly different at or below the 1% level
*Significantly different at the 5% level
Panelists rated sliced portions of berries after fruit had been in cold storage 4 to 5 days and panelists were not able to identify varieties being rated. Flavor ratings are between 1 and 5 - 5 being best.

TABLE #3

1992 FLY RANCH TIME OF PLANTING FLAVOR TEST SUMMARY

| EVAL DATE | # OF EVALUATORS | LEVEL OF SIGN. | AVERAGE FLAVOR SCORE 'X13' | COMMANDER | SWEDE |
|---|---|---|---|---|---|
| 06/03/92 | 17 | 0.639 | 3.7 | 3.6 | 3.8 |
| 07/01/92 | 16 | 0.002** | 3.6 a | 2.6 b | 3.5 a |
| 07/15/92 | 12 | 0.341 | 3.0 | 3.5 | 3.3 |
| 07/22/92 | 11 | 0.001** | 3.5 a | 2.3 b | 3.0 a |
| 08/05/92 | 13 | 0.089 | 3.4 | 2.9 | 2.8 |
| 08/12/92 | 11 | 0.488 | 3.5 | 3.1 | 3.1 |
| 08/18/92 | 7 | 0.707 | 3.1 | 3.1 | 3.5 |
| 08/27/92 | 10 | 0.392 | 3.4 | 2.9 | 3.0 |
| 09/02/92 | 6 | 0.611 | 3.3 | 3.3 | 2.8 |
| 09/09/92 | 14 | 0.101 | 3.6 | 3.0 | 3.5 |
| 09/22/92 | 15 | 0.025* | 3.5 a | 2.9 b | 3.5 a |
| 10/07/92 | 11 | 0.001** | 3.0 b | 2.8 b | 4.0 a |
| | | AVERAGE: | 3.4 | 3.0 | 3.3 |

**Significantly different at or below the 1% level
*Significantly different at the 5% level
Panelists rated sliced portions of berries after fruit had been in cold storage 4 to 5 days and panelists were not able to identify varieties being rated. Flavor ratings are between 1 and 5 - 5 being best.

TABLE #4

PRODUCTION AND FRUIT SIZE
1993 FLY RANCH TIME OF PLANTING,
WATSONVILLE, CALIFORNIA

| PLOT | VARIETY | NURSERY | DIG DATE | PLANTING DATE |
|---|---|---|---|---|
| 4205 | 'X13' | McA | 10/19/92 | 11/05/92 |

| | 1993 APR | MAY | JUN | JUL |
|---|---|---|---|---|
| NUMBER OF PICKS | 6 | 8 | 9 | 9 |
| GRAMS/PLANT | 103 | 204 | 228 | 285 |
| AVE. BERRY WT (gms./berry) | 24.6 | 35.6 | 25.6 | 21.0 |

| | 1993 AUG | SEP | OCT | TOTAL |
|---|---|---|---|---|
| NUMBER OF PICKS | 8 | 7 | 1 | 48 |
| GRAMS/PLANT | 177 | 255 | 19 | 1271 |
| AVE. BERRY WT (gms./berry) | 21.6 | 21.3 | 21.7 | |

| PLOT | VARIETY | NURSERY | DIG DATE | PLANTING DATE |
|---|---|---|---|---|
| 5001 | SWEDE | McA | 10/19/92 | 11/12/92 |

| | 1993 APR | MAY | JUN | JUL |
|---|---|---|---|---|
| NUMBER OF PICKS | 6 | 8 | 9 | 9 |
| GRAMS/PLANT | 147 | 201 | 451 | 405 |
| AVE. BERRY WT (gms./berry) | 27.5 | 40.6 | 31.5 | 23.4 |

| | 1993 AUG | SEP | OCT | TOTAL |
|---|---|---|---|---|

TABLE #4-continued

PRODUCTION AND FRUIT SIZE
1993 FLY RANCH TIME OF PLANTING,
WATSONVILLE, CALIFORNIA

| | | | | |
|---|---|---|---|---|
| NUMBER OF PICKS | 9 | 8 | 1 | 50 |
| GRAMS/PLANT | 236 | 285 | 38 | 1763 |
| AVE. BERRY WT (gms./berry) | 23.6 | 26.7 | 24.2 | |

Production and size yield data is from marketable berries only. This fruit is from plants that are winter planted and in the first year production. McA is a high elevation nursery.

TABLE #5

'X13' Isozyme banding patterns
compared to 'Swede' and 'Commamder' and 'Joe Reiter'

| CULTIVAR | PG1 | LAP | PGM |
|---|---|---|---|
| 'X13' | A2 | B3 | C4 |
| 'SWEDE' | A1 | B3 | C2 |
| 'COMMANDER' | A4 | B3 | C4 |
| 'JOE REITER' | A4 | B3 | C4 |

TABLE #6

Leaf Characteristics of 'X13' and 'Swede'
- Watsonville, California
10/7/93

| | SERRATION DEPTH mm* | PETIOLE LENGTH cm** |
|---|---|---|
| 'X13' | 5.1 | 19.0 |
| 'SWEDE' | 5.1 | 13.1 |

*= Measuring from serration apex to a line between where serrations join.
**= Measuring from petiolule to lowest point of basal bract.

TABLE #7

AVERAGE PLANT SIZE -
Watsonville, California
9-17-93

Width - Leaf tip to leaf tip - centimeters
Height - Soil to top leaf - centimeters
(Plants grown over 8" plastic covering drip irrigation).

| 'X13' | | 'SWEDE' | |
|---|---|---|---|
| W | H | W | H |
| 41.7 | 31.4 | 36.6 | 25.3 |

We claim:

1. The new distinct and variety of strawberry plant herein described and illustrated, and identified by the characteristics enumerated above.

* * * * *